United States Patent
Roth et al.

(10) Patent No.: US 8,236,081 B2
(45) Date of Patent: *Aug. 7, 2012

(54) PERMEABLE MEMBRANE WATER DISSIPATION DEVICE

(75) Inventors: Gary James Roth, Wake Forest, NC (US); Daniel Patrick Dwyer, Raleigh, NC (US)

(73) Assignee: Teleflex Medical Incorporated, Research Triangle Park, NC (US)

( * ) Notice: Subject to any disclaimer, the term of this patent is extended or adjusted under 35 U.S.C. 154(b) by 963 days.

This patent is subject to a terminal disclaimer.

(21) Appl. No.: 11/826,597

(22) Filed: Jul. 17, 2007

(65) Prior Publication Data
US 2009/0020124 A1    Jan. 22, 2009

(51) Int. Cl.
*B01D 46/00* (2006.01)
(52) U.S. Cl. ............... 55/498; 55/309; 55/312; 55/314; 55/DIG. 33; 55/DIG. 34; 128/205.29; 128/205.27; 128/203.16
(58) Field of Classification Search .......... 96/108, 96/124, 125, 150, 4; 55/309, 312, 314, DIG. 33, 55/DIG. 34, 498; 95/46, 52; 128/205.29, 128/205.27, 203.16, 202.13; 261/104, 107
See application file for complete search history.

(56) References Cited

U.S. PATENT DOCUMENTS

| | | | |
|---|---|---|---|
| 3,747,598 A | 7/1973 | Cowans | |
| 4,172,709 A | 10/1979 | Kippel et al. | |
| 4,200,094 A | 4/1980 | Gedeon et al. | |
| 4,232,667 A * | 11/1980 | Chalon et al. | 128/203.26 |
| 4,355,636 A * | 10/1982 | Oetjen et al. | 128/204.13 |
| 4,381,267 A * | 4/1983 | Jackson | 261/104 |
| 4,548,626 A | 10/1985 | Ackley et al. | |
| 4,771,770 A | 9/1988 | Artemenko et al. | |
| 4,897,359 A * | 1/1990 | Oakley et al. | 435/297.4 |
| 5,035,236 A | 7/1991 | Kanegaonkar | |
| 5,195,527 A | 3/1993 | Hicks | |
| 5,230,727 A | 7/1993 | Pound et al. | |
| 5,460,172 A | 10/1995 | Eckerbom et al. | |
| 5,505,768 A | 4/1996 | Altadonna | |
| 6,415,788 B1 | 7/2002 | Clawson et al. | |
| 6,550,476 B1 | 4/2003 | Ryder | |
| 6,792,946 B1 | 9/2004 | Waldo, Jr. et al. | |
| 6,976,488 B2 * | 12/2005 | Halperin | 128/201.13 |

(Continued)

FOREIGN PATENT DOCUMENTS

| | | |
|---|---|---|
| FR | 2692153 A1 | 12/1993 |
| GB | 2267661 A | 12/1996 |
| WO | WO 99/60954 A1 | 12/1999 |
| WO | WO 2005/047797 A2 | 5/2005 |

OTHER PUBLICATIONS

Extended European Search Report of EP 08 77 2247 dated Jun. 18, 2012.

*Primary Examiner* — Jason M Greene
*Assistant Examiner* — Karla Hawkins
(74) *Attorney, Agent, or Firm* — Baker & Hostetler LLP

(57) ABSTRACT

An embodiment in accordance with the present invention provides a water dissipation device to remove water vapor from a humidified gas traveling through a breathing circuit between a patient and a ventilator, or a ventilator and a patient. The present invention includes a water dissipation device having a housing defining entry and exit ports for coupling to the breathing circuit and a breathable medium permeable to water vapor and impermeable to liquid water bacteria, viruses and other gases enclosed within said housing.

8 Claims, 12 Drawing Sheets

U.S. PATENT DOCUMENTS

| | | |
|---|---|---|
| 7,140,366 B2 | 11/2006 | Smith et al. |
| 2001/0054422 A1 | 12/2001 | Smith et al. |
| 2002/0002976 A1* | 1/2002 | Smith et al. .............. 128/203.16 |
| 2003/0085165 A1* | 5/2003 | Shane ............................ 210/85 |
| 2004/0123974 A1 | 7/2004 | Marler et al. |
| 2005/0103339 A1* | 5/2005 | Daly et al. ............... 128/204.18 |

* cited by examiner

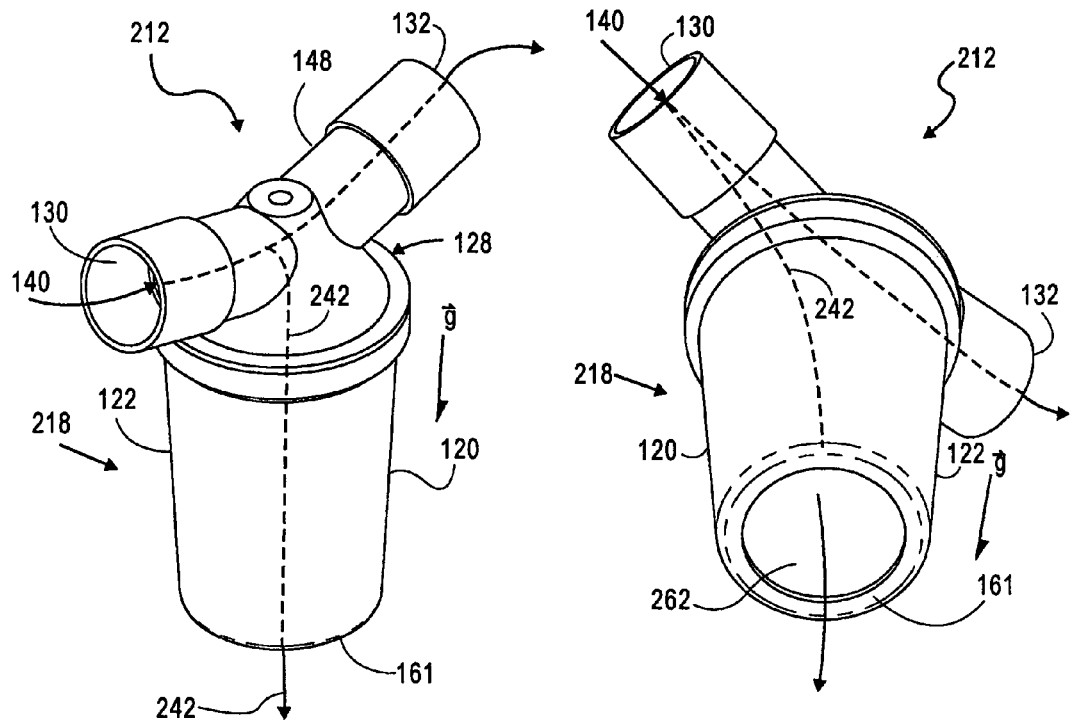
FIG. 9
FIG. 10
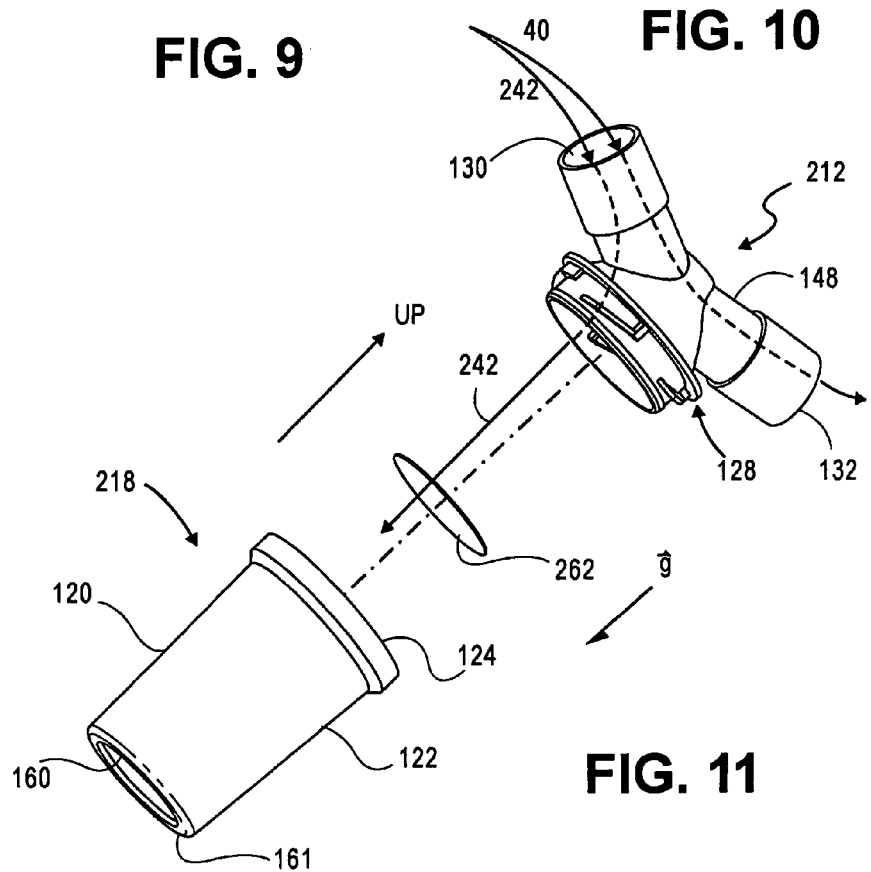
FIG. 11

PERMEABLE MEMBRANE WATER DISSIPATION DEVICE

FIELD OF THE INVENTION

The present invention relates generally to a medical device. More particularly, the present invention is related to a water dissipation device for placement in a breathing circuit.

BACKGROUND

A breathing circuit delivers medical gas to a patient under pressure in a prescribed volume and breathing rate. The medical gas is often humidified by a humidifier located at or near the ventilator or respirator. The optimum respiratory circuit delivers 100% RH medical gases@35 to 39 Degrees C. to the patient while reducing the amount of humidity and subsequent condensate delivered back to the ventilator through the expiratory limb. Therefore, the humidified gas has to travel through all or most of the tubing and has time to cool. Cooling of the gas leads to rainout or condensation in the breathing tube and collection of water within the breathing circuit.

Several solutions to the problem of rainout have been developed. One such solution is a heating wire provided along the length of the tube. The wire may be provided within the interior of the tubing or alternatively may be embedded along the interior of the tubing. The wire heats the humidified gas traveling through the tubing to prevent the gas from cooling, thus preventing the problem of water condensing out of the gas traveling through the breathing circuit. However, the manufacture of such heated wire respiratory circuits can be time consuming and costly.

Another such solution, which eliminates the heated wire, is to provide a water collection device somewhere within the breathing circuit. A water collection apparatus is typically placed in the expiratory limb of the respiratory circuit in front of the ventilator or respirator to collect and manually remove excessive condensation prior to the gases entering the ventilator or respirator. It is known that excessive condensate entering a ventilator or respirator from the expiratory limb of a respiratory circuit can harm the device.

Most frequently, the water collection device is designed to trap the condensed water vapor in a removable container. When the container is removed, a valve can be actuated to create a gas tight seal for the breathing circuit. However, this type of water collection device has to be monitored and manually emptied, causing risk of patient or caregiver infection.

Accordingly, it is desirable to provide an improved apparatus for removing or decreasing water vapor or condensate in a breathing circuit. It is further desirable that the improved apparatus for removing water vapor or condensate from the breathing tube reduce or eliminate the need to heat the exhalation limb of the breathing tube and the need to use currently known water collection or other dissipation devices.

SUMMARY

The foregoing needs are met, to a great extent, by the present invention, wherein in one aspect an apparatus is provided that in some embodiments provides an improved water dissipation device for placement in a breathing circuit where said water dissipation device will eliminate the need to use a secondary water collection device or manually remove the water condensate and will instead allow for removal of water vapor from the circuit through osmosis.

In one embodiment of the present invention, a water dissipation device for a breathing circuit is provided, including a housing having a cylindrical bottom container having a side wall. The side wall defines a top opening. A lid is mounted on the top opening. The housing defines an entry port and an exit port for coupling to a breathing circuit and defining a first flow path between said entry and exit port. A breathable medium is enclosed in said housing. The housing defines a second flow path from the entry port of the housing through the tubular breathable medium to exit the housing from at least one opening other than the exit port.

In another embodiment of the present invention, a water dissipation device for a breathing circuit is provided, having a cylindrical caged body enclosing an annular breathable medium. A first end portion defines an entry port coupled to a first side of said caged body. A second end portion defines an exit port coupled to a second side of said caged body. The cylindrical caged body defines a first flow path between the entry port and the exit port. The cylindrical caged body defines a second flow path from the entry port through the annular breathable medium and the cylindrical caged housing.

In yet another aspect of the present invention, a water dissipation device for a breathing circuit is provided, having a housing having a cylindrical bottom container having a side wall defining a plurality of windows. A lid is mounted on the cylindrical bottom container. The housing defines an entry port and an exit port for coupling to a breathing circuit and defining a first flow path between said entry and exit ports. A breathable medium is enclosed in said housing and the housing defines a second flow path from the entry port of the housing through the tubular breathable medium to exit the housing from at least one of the plurality of windows.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 9 is a three-quarter view illustrating another embodiment of the present invention;

FIG. 10 is a bottom view of the embodiment illustrated in FIG. 9;

FIG. 11 is an exploded view of the embodiment illustrated in FIGS. 9 and 10;

DETAILED DESCRIPTION

Figure 1:
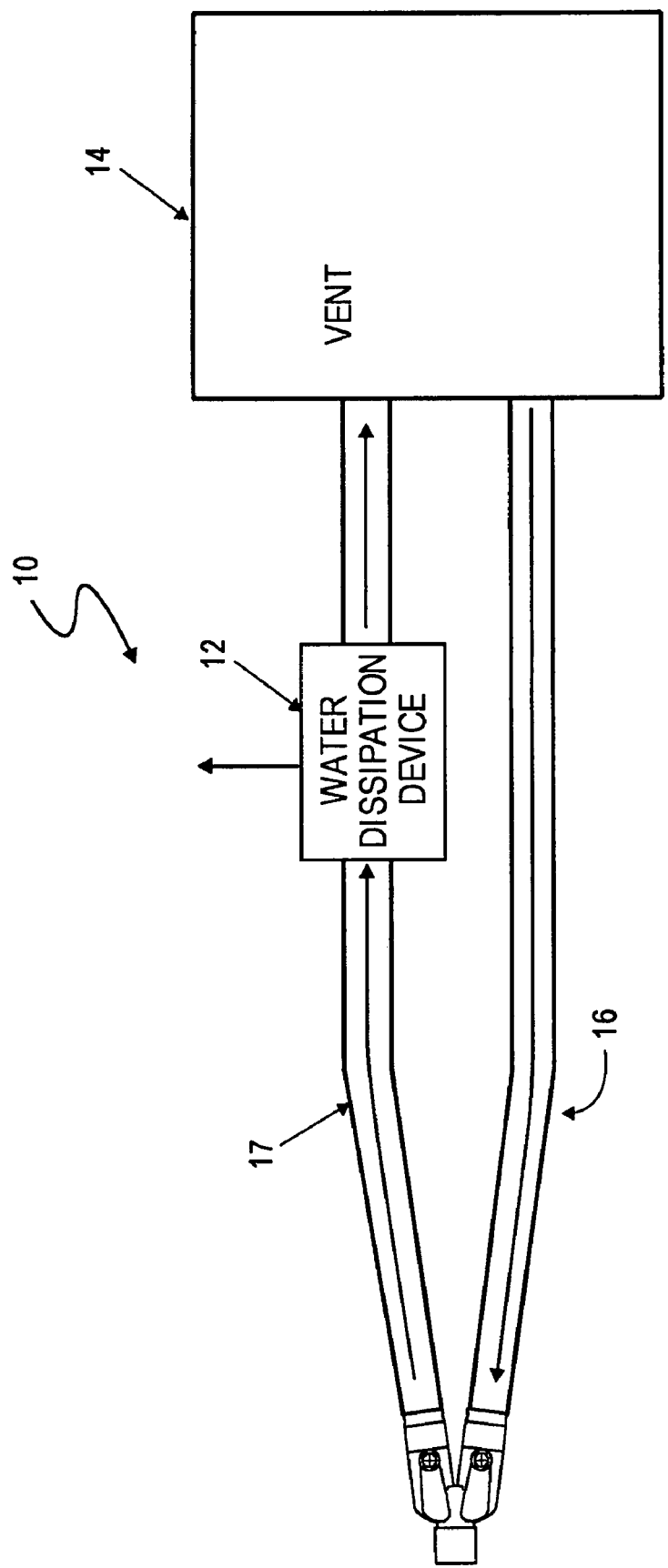
FIG. 1 is a schematic view illustrating a breathing circuit.

The invention will now be described with reference to the drawing figures, in which like parts are referred to with like reference numerals throughout. An embodiment in accordance with the present invention provides a water dissipation device to remove water vapor or condensate from a humidified medical gas traveling through a breathing circuit between a ventilator and a patient or the patient and the ventilator. The present invention includes a water dissipation device having a housing defining entry and exit ports for coupling to the breathing circuit and a breathable medium permeable to water vapor and impermeable to liquid water, viruses and bacteria enclosed within said housing.

FIG. 1 is a schematic view illustrating a breathing circuit 10 including a water dissipation device 12. The water dissipation device 12 is placed in the breathing circuit 10 between a ventilator 14 and a breathing tube 17 from a patient. The breathing circuit 10 is completed by a second breathing tube 16 extending between the patient and the ventilator. The breathing circuit 10 is a closed system wherein liquid water and/or gases are not able to enter or leave the breathing circuit, except for the release of water vapor. Therefore, the breathing circuit 10 is a closed system except with regard to the passage of water vapor.

Figure 2:
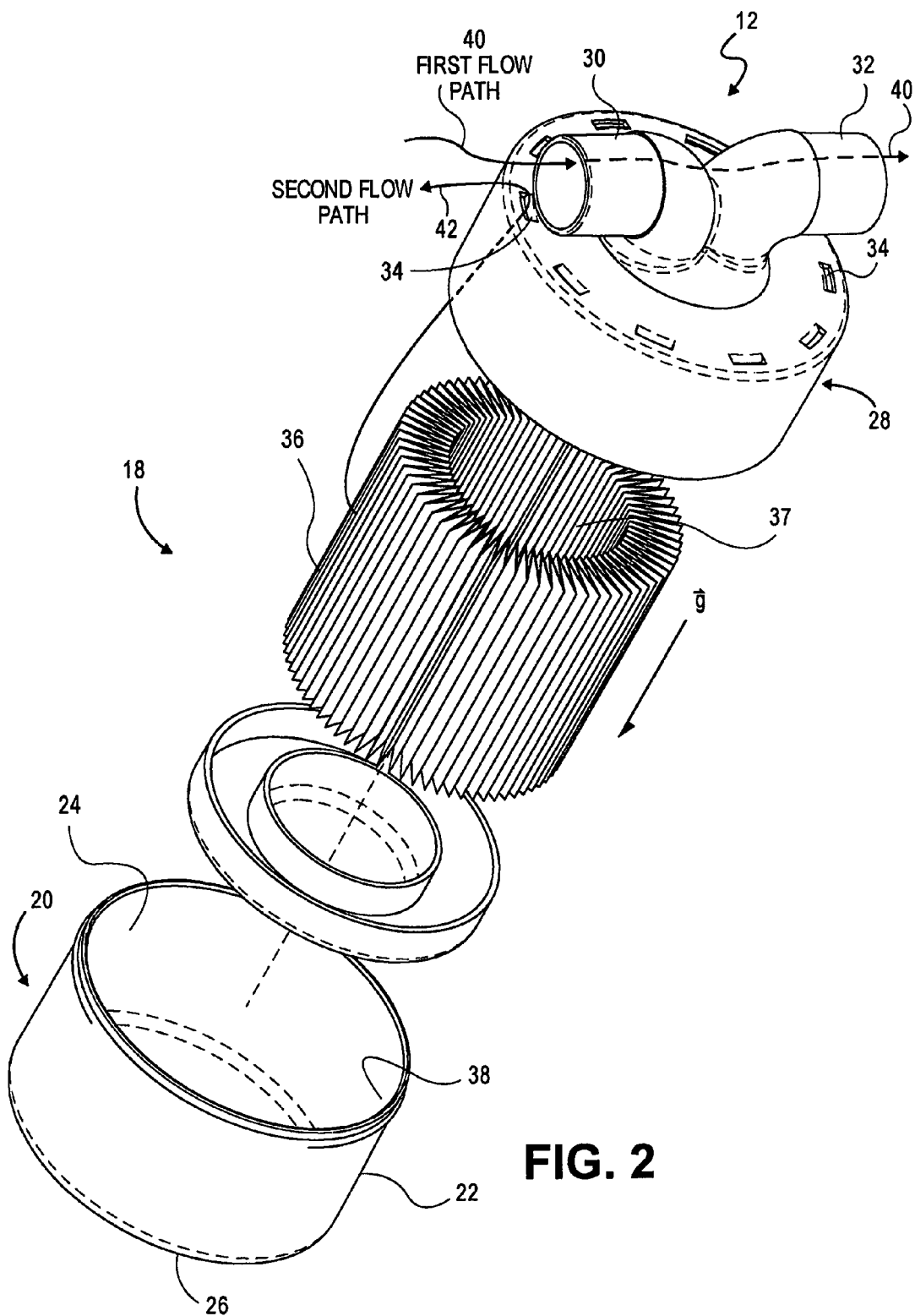
FIG. 2 is an exploded view illustrating a water dissipation device according to an embodiment of the invention.

An embodiment of the present invention is illustrated in FIG. 2. FIG. 2 is an exploded view illustrating the water dissipation device 12 according to a preferred embodiment of the invention. The water dissipation device 12 includes a housing 18 having a cylindrical bottom container 20. The cylindrical bottom container 20 has a side wall 22 that defines a top opening 24 and a bottom surface 26. Also included in the housing 18 is a lid 28 mounted over the top opening 24. The housing 18 defines an entry port 30 and an exit port 32, and more specifically the lid 28 defines the entry port 30 and the exit port 32. The entry port 30 and the exit port 32 allow the water dissipation device 12 to be connected to a breathing circuit, such that the entry port 30 is connected to an expiratory limb of a breathing tube from the patient and the exit port 32 is connected to the rest of the same breathing tube directed toward a ventilator. As shown in FIG. 2, water vapor vents 34 are defined by the housing 18, and more specifically are defined along a periphery of the lid 28. A plurality of the water vapor vents 34 are disposed around an outer edge of a top surface of the lid 28. The lid 28 can also be manufactured from a thermally conductive material to facilitate the cooling of the respiratory gases and increase water condensation, An annular or tubular breathable medium 36 is enclosed in the housing 18. The tubular breathable medium 36 may be pleated to increase the surface area of the breathable medium within the housing 18. The breathable medium 36 may also line at least a portion of an inside surface 38 of the side wall 22. As used herein, a "breathable medium" is formed of a material that is permeable to water vapor and impermeable to liquid water and gases other than water vapor. The breathable medium 36 allows water vapor to exit the water dissipation device while eliminating the need to open the water dissipation device to empty a reservoir of water and, therefore, allows the system to remain closed.

Figure 3:
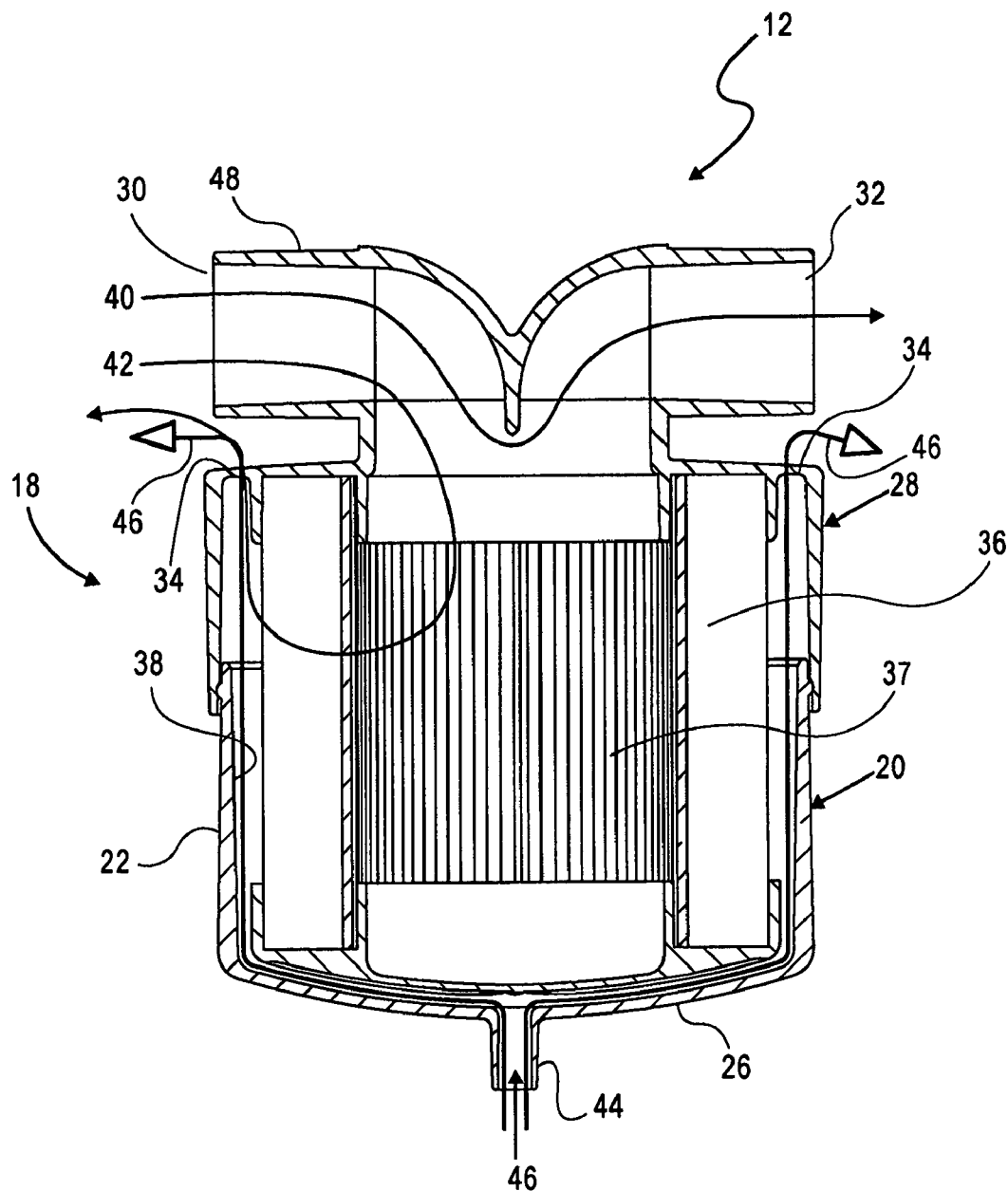
FIG. 3 is a cross sectional view illustrating the embodiment of the water dissipation device illustrated in FIG. 2.

FIG. 3 is a cross sectional view that further illustrates the embodiment of the water dissipation device illustrated in FIG. 2. The housing 18 defines a first flow path 40 of humidified gas between the entry port 30 and the exit port 32. In the first flow path 40, the humidified gas travels into the water dissipation device 12 via the entry port 30, through the housing 18 and exits the water dissipation device 12 via the exit port 32. The first flow path 40 therefore generally corresponds to the main flow path through the water dissipation device along the breathing circuit.

The housing also defines a second flow path 42 for water vapor that extends from the entry port 30 through the tubular breathable medium 36 to at least one opening defined by the housing, other than the exit port 32. In the embodiment shown in FIGS. 2 and 3, this at least one opening includes the water vapor vents 34 defined by the lid of the housing 18. As shown in FIGS. 2 and 3, in the second flow path 42, water vapor in the humidified gas may permeate through breathable medium 36 and exit through the water vapor vents 34. However, liquid water and other gases cannot permeate the breathable medium 36 and exit through the water vapor vents 34.

Additionally, the bottom surface 26 of the outer housing 18 defines an orifice 44 to connect the water dissipation device 12 to an input air source. The housing 18, therefore, defines a third flow path 46 from the orifice 44 through the water dissipation device 12 and out through the water vapor vents 34. The third flow path 46 provides a route for air introduced by the auxiliary compressed dry air input source to blow condensation off of the breathable medium to reduce liquid water collecting in the water dissipation device, and increase the efficiency of the breathable permeable medium. As can be seen in FIG. 2, the annular or tubular breathable medium 36 defines a central channel 37 within which the second flow path 42 may follow.

Figure 4:
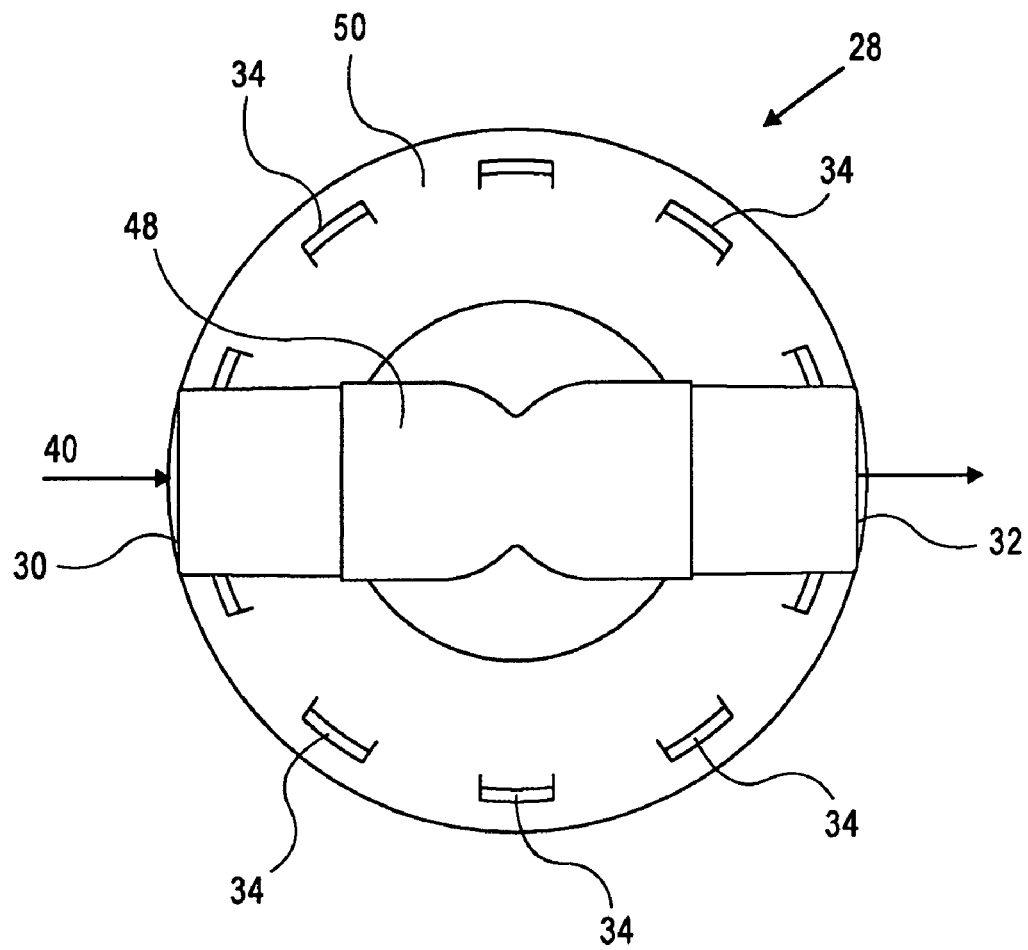
FIG. 4 is a top view of the embodiment of the water dissipation device illustrated in FIGS. 2 and 3.

FIG. 4 is a top view of the lid 28 of the embodiment of the water dissipation device illustrated in FIGS. 2 and 3. FIG. 4 illustrates the entry port 30 and exit port 32 and the water vapor vents 34 in more detail. The entry port 30 and the exit port 32 are disposed on a top surface of the lid 28 and the lid 28 defines a tubular connector portion 48 that couples the water dissipation device 12 to a breathing tube 16. In this embodiment multiple water vapor vents 34 are disposed around the outer edge of the lid 28. However, it is important to note that the number and placement of the water vapor vents 34 are not limited by this embodiment and there may be any number of water vapor vents 34 disposed in any position on the lid 28 or on the remainder of the housing 18.

Figure 5:
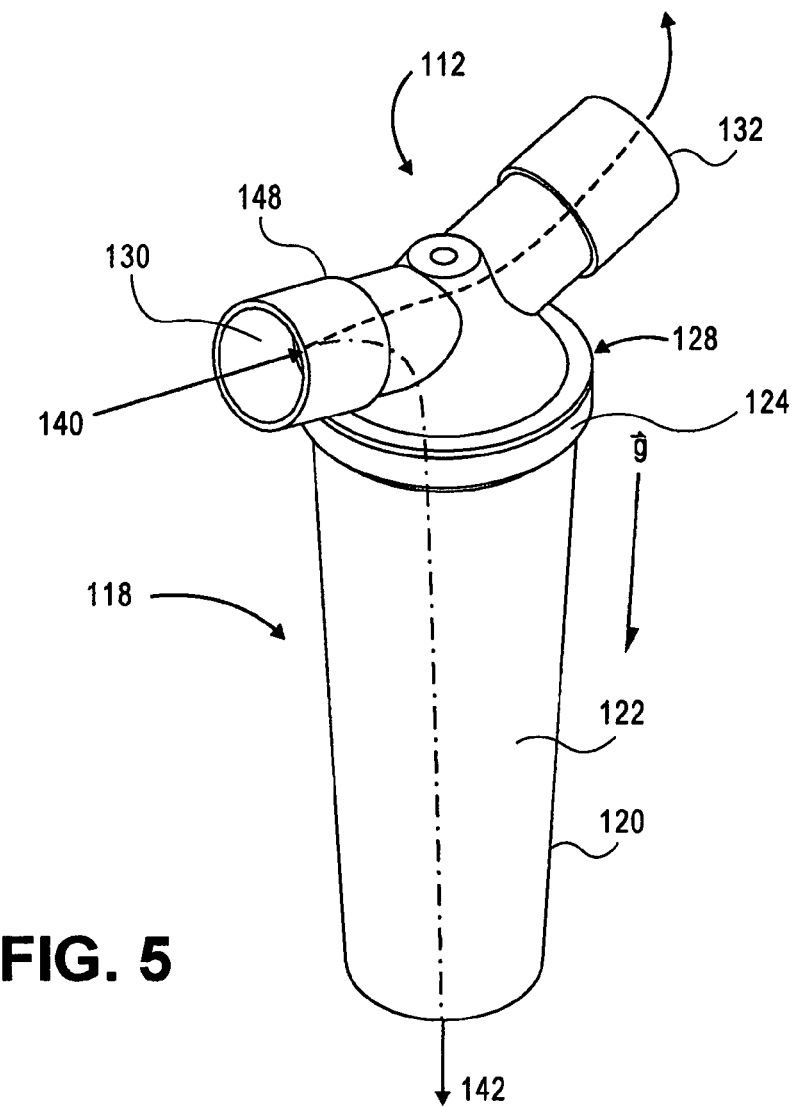
FIG. 5 is a three-quarter view illustrating the water dissipation device according to another embodiment of the present invention.

Another embodiment of the present invention is illustrated in FIG. 5. FIG. 5 is a three-quarter view illustrating a water dissipation device 112 according to another embodiment of the present invention. In this embodiment, the housing 118 includes a cylindrical bottom container 120 that has side wall 122 defining a top opening 124. The housing also includes a lid 128 that is mounted on the top opening 124. Additionally, the housing 118 defines an entry port 130 and an exit port 132.

Figure 6:
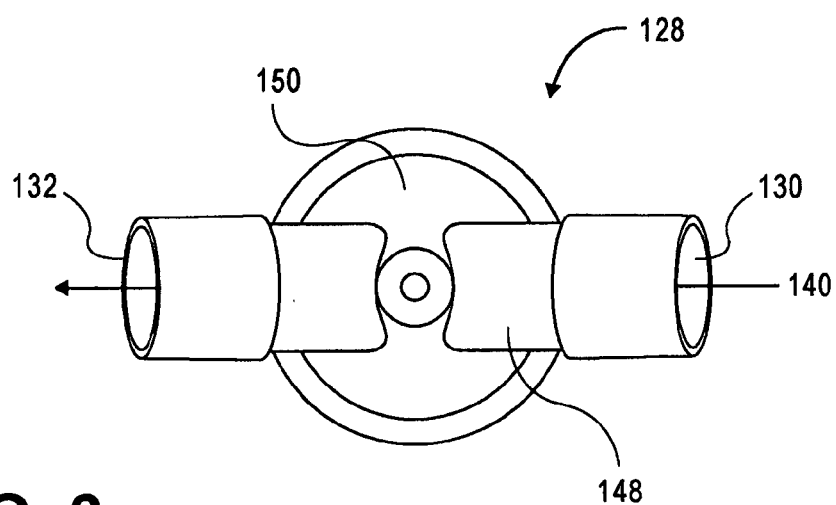
FIG. 6 is a top view of the embodiment illustrated in FIG. 5.

FIG. 6 is a top view of the embodiment illustrated in FIG. 5. FIG. 6 illustrates in more detail the lid 128 and the entry port 130 and the exit port 132. Preferably, the lid 128 is the portion of the housing that defines the entry port 130 and the exit port 132. The entry port 130 and the exit port 132 are disposed on the top surface 150 of the lid 128 and include a tubular connector portion 148 that couples the water dissipation device 112 to a breathing tube.

Figure 7:
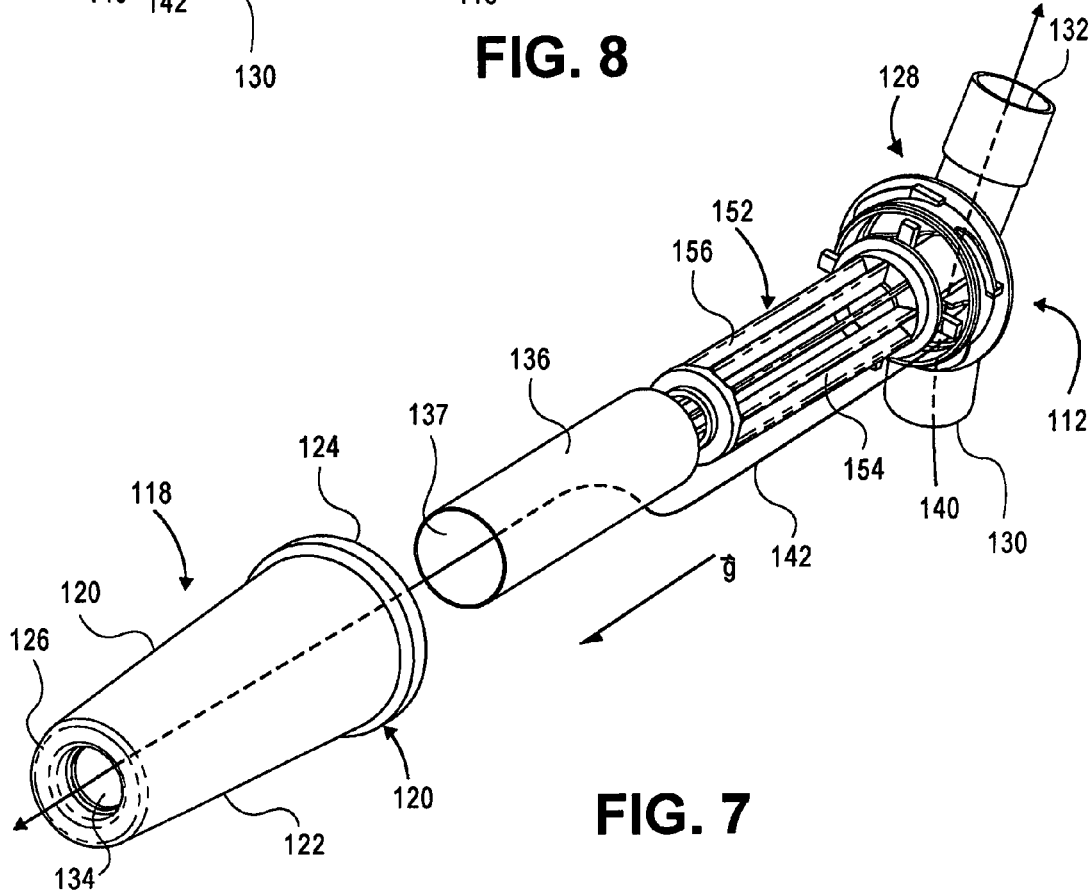
FIG. 7 is an exploded view of the embodiment illustrated in FIGS. 5 and 6.

FIG. 7 is an exploded view of the embodiment illustrated in FIGS. 5 and 6. FIG. 7 illustrates in more detail the structure of the housing 118 and the tubular breathable medium 136. Threads on the lid 128 as well as corresponding threads on the cylindrical bottom container 120 couple the lid 128 to the cylindrical bottom container 120, such that there is an air tight seal between them.

Additionally, the lid 128 has a tubular cage 152 that extends into the cylindrical bottom container 120 of the housing 118. The tubular cage 152 has fins 154 that extend along the span of the housing 118. The fins 154 are separated by longitudinal openings or spaces that define water vapor vents 156 between the fins 154. An annular or tubular breathable medium 136 is also disposed within the cylindrical bottom container 120, and it is positioned between the tubular cage 152 and the sidewalls 122 of the cylindrical bottom container 120 of the outer housing 118.

Figure 8:
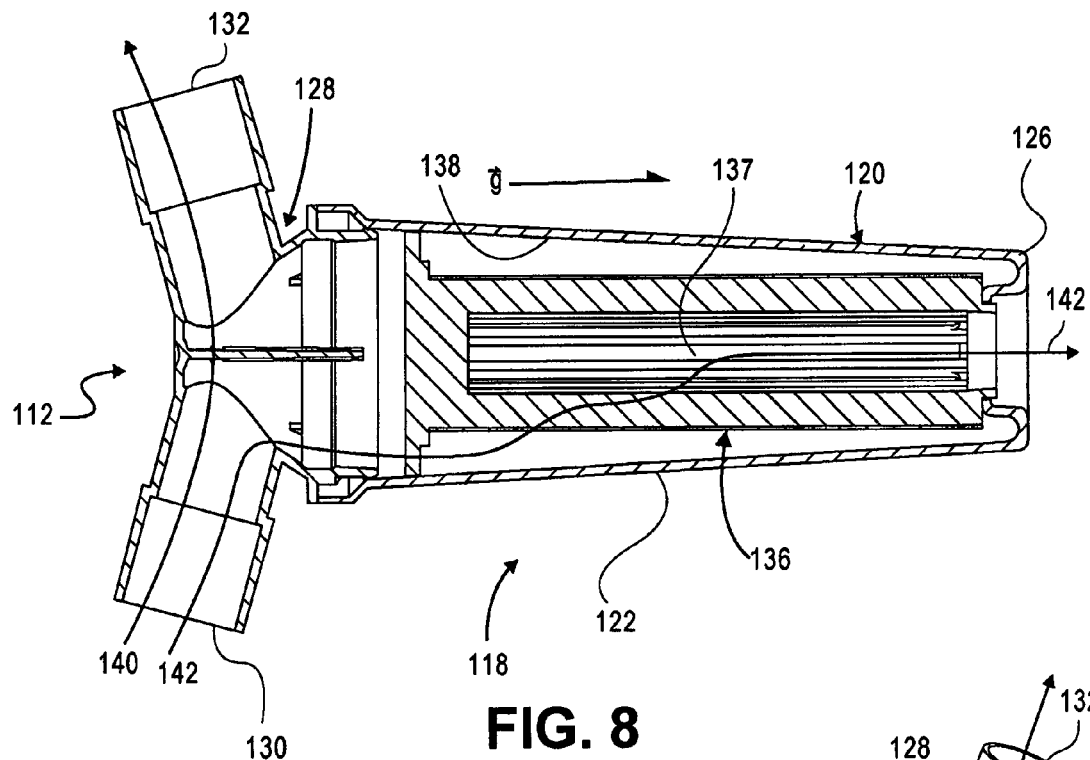
FIG. 8 is a cross sectional view of the embodiment illustrated in FIGS. 5-7.

FIG. 8 is a cross sectional view of the embodiment illustrated in FIGS. 5 through 7. FIG. 8 illustrates the housing 118 and the breathable medium 136 in a fully assembled condition. The lid 128 and the cylindrical bottom container 120 couple together to form an air tight seal. With reference to the gravity vector g shown in FIGS. 7 and 8 for the preferred orientation of the device 112 when inserted into a breathing circuit, the tubular cage 152 extends from a bottom surface of the lid 128 to the bottom surface 126 of the cylindrical bottom container 120. The tubular breathable medium 136 is disposed around and supported by the tubular cage 152.

A first flow path 140 is defined by the housing 118 and extends through the water dissipation device 112 directly from the entry port 130 and through to the exit port 132 as shown in FIGS. 7 and 8. The humidified gas generally flowing through the breathing circuit to which the device of the present invention is attached can therefore travel through the water dissipation device 112 via the first flow path 140. A second flow path 142 is also defined by the housing 118 and extends from the entry port 130 through the tubular breathable medium 136 and out of the water dissipation device 112 via the water vapor vents 156 defined by the fins 154 of the tubular cage 152. Water vapor in the humidified gas may permeate the breathable medium 136 to exit through the water vapor vents 156, but liquid water, bacteria, viruses and other gases cannot permeate the breathable medium 136. It will be noted in FIGS. 7-8 that the second flow path provides for water vapor permeation from the outer surface to the inner surface of the tubular breathable medium 136. Breathable medium 136 defines a central channel 137 through which the final portion of the second flow patent 142 flows.

FIGS. 9, 10 and 11 illustrate another embodiment of the water dissipation device of the present invention. In this embodiment, the housing 218 defines the entry port 130 and exit port 132 for coupling a water dissipation device 212 to a breathing circuit. Preferably, in this embodiment, the housing 218 has a cylindrical bottom container 120 having a side wall 122 that defines a top opening 124. The lid 128 is mounted on the top opening 124 and preferably defines the entry port 130 and the exit port 132. The housing 218 also defines an opening 160 in a bottom surface 161 of the housing 218. A flat disk breathable medium 262 is disposed in said housing 218 and covers the opening 160 in the bottom surface of the housing 218.

A first flow path 140 between the entry port 130 and the exit port 132 is defined by the housing 218. The housing 218 also defines a second flow path 242 from the entry port 130 through the housing 218 and out through the opening 160 and flat disk breathable medium 262 on the bottom surface 161 of the cylindrical bottom container 120. Only water vapor passes through the flat disk breathable medium 262 because it is permeable to water vapor but impermeable to liquid water, bacteria, viruses and other gases.

Figure 12:
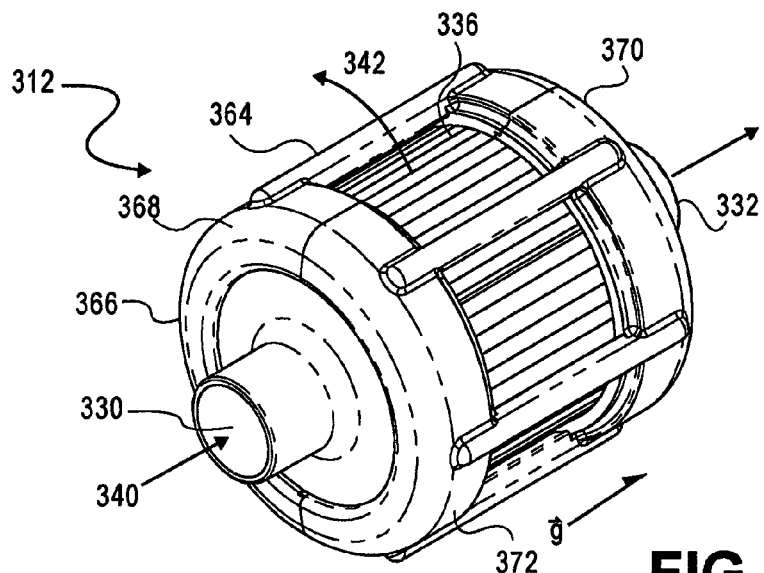
FIG. 12 is a side view illustrating another embodiment of the present invention.
Figure 13:
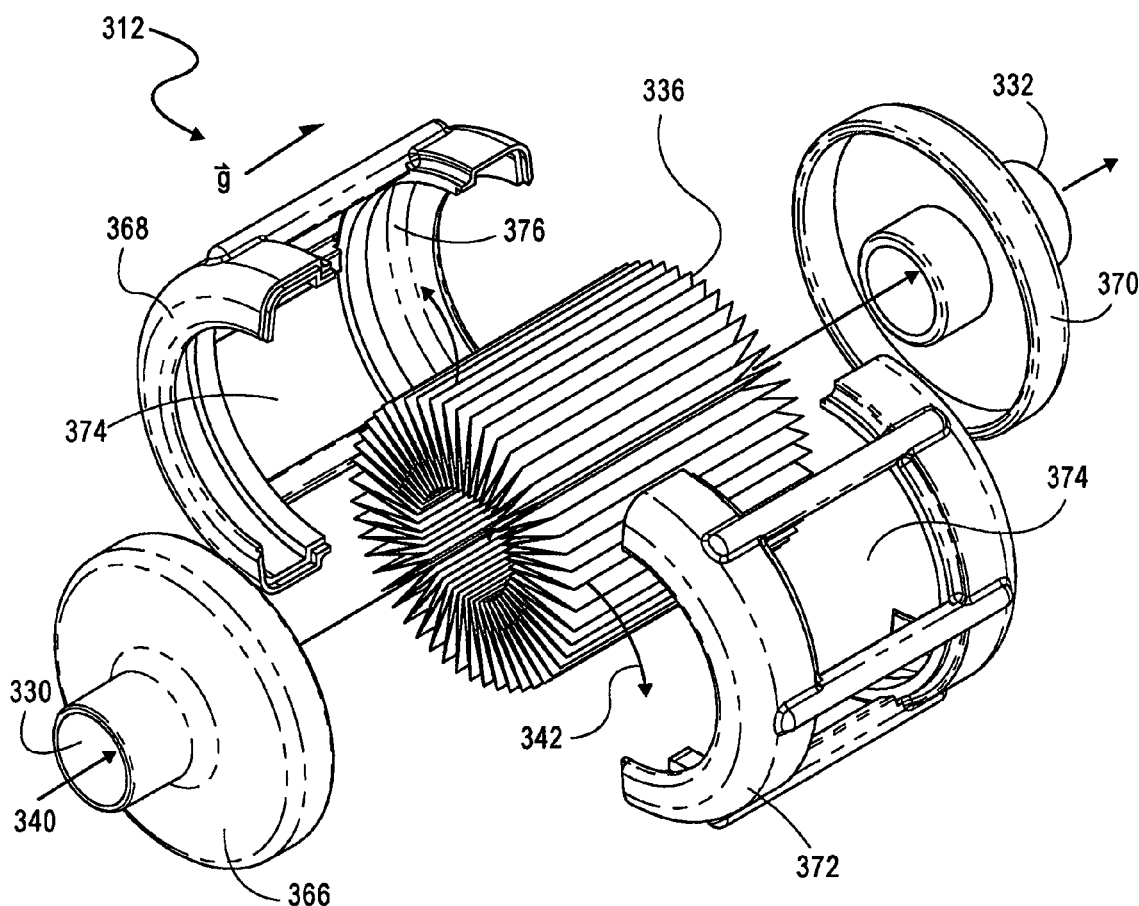
FIG. 13 is an exploded view of the embodiment illustrated in FIG. 12.

FIG. 12 illustrates a side view of another embodiment of the water dissipation device of the present invention. FIG. 13 illustrates an exploded view of the embodiment illustrated in FIG. 12. In this embodiment, a water dissipation device 312 has a cylindrical caged body 364 that encloses an annular or tubular breathable medium 336. The cylindrical caged body 364 is formed of two halves 368 and 372, which can be separable. The water dissipation device 312 has a first end cap 366 defining the entry port 330. A second end portion 370 defines the exit port 332. The circular end caps 366 and 370 are held in place inside complementary grooves on the inside of portions of the caged body halves 368 and 372. A plurality of windows 374 are defined by the cylindrical caged body 364 to allow for egress of water vapor from the water dissipation device 312.

The cylindrical caged body 364 encloses a tubular breathable medium 336 which lines at least a portion of an inside surface 376 of the cylindrical caged body 364. Preferably, the tubular breathable medium 336 is pleated and permeable to water vapor but impermeable to liquid water, bacteria, viruses and other gases. However, the breathable medium 36 should not be limited by this description and may take various forms or positions within the cylindrical caged body 364.

The cylindrical caged body 364 defines a first flow path 340 between the entry port 330 and the exit port 332. Additionally, the cylindrical caged body 364 defines a second flow path 342 from the entry port 330, through the breathable medium 336 and out of the water dissipation device 312 via the windows 374 in the cylindrical caged body 364. Only water vapor passes through the tubular breathable medium 36 in the second flow path 342.

Figure 14:
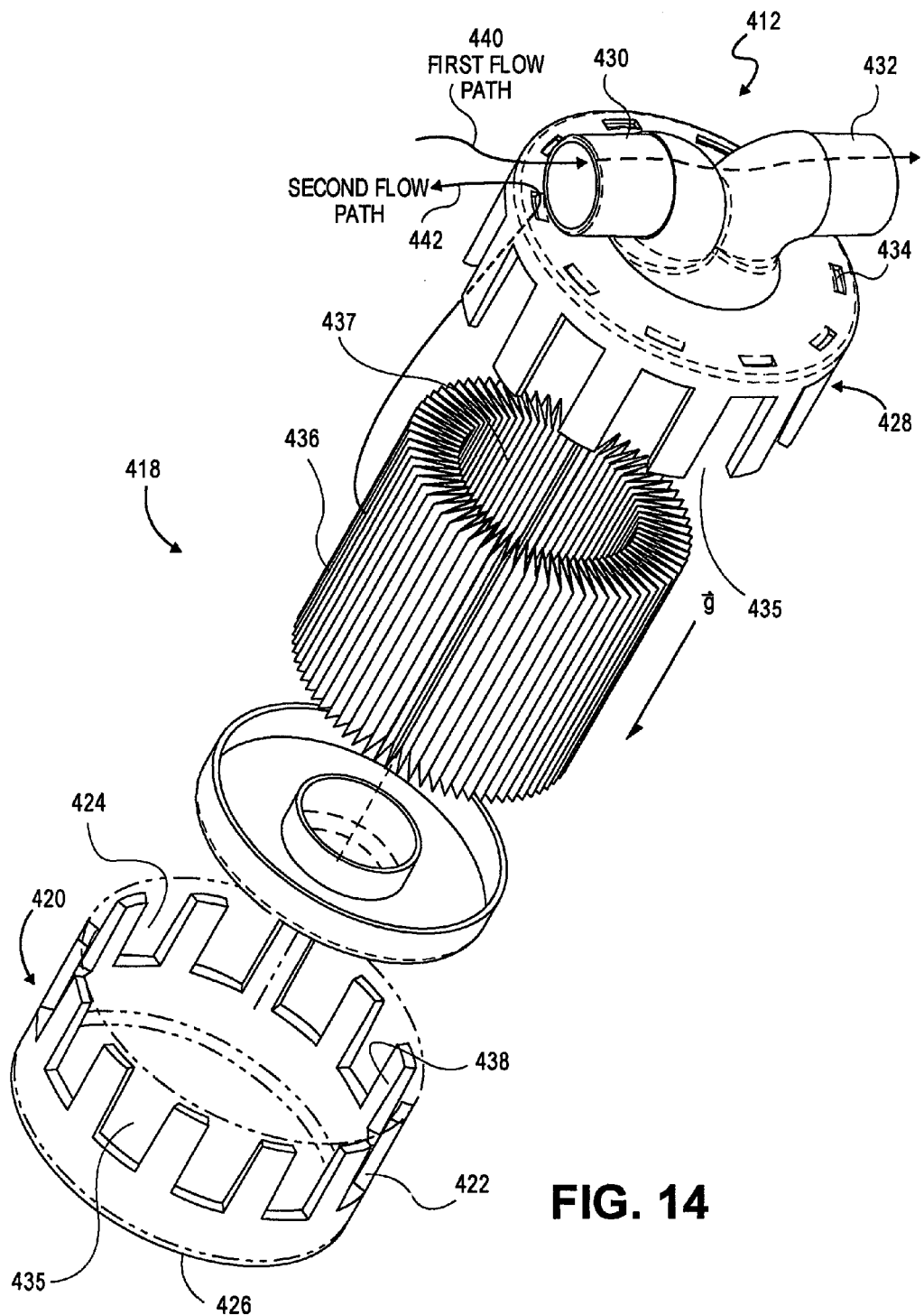
FIG. 14 is an exploded view illustrating another embodiment of the present invention.

An embodiment of the present invention is illustrated in FIG. 14. FIG. 14 is an exploded view illustrating the water dissipation device 412 according to a preferred embodiment of the invention. The water dissipation device 412 includes a housing 418 having a caged cylindrical bottom container 420. The caged cylindrical bottom container 420 has a side wall 422 that defines a top opening 424 and a bottom surface 426. Also included in the housing 418 is a lid 428 mounted over the top opening 424. The housing 418 defines an entry port 430 and an exit port 432, and more specifically the lid 428 defines the entry port 430 and the exit port 432. The entry port 430 and the exit port 432 allow the water dissipation device 412 to be connected to a breathing circuit, such that the entry port 430 is connected to an expiratory limb of a breathing tube from the patient and the exit port 432 is connected to another tube directed toward a ventilator. As shown in FIG. 14, water vapor vents 434 are defined by the housing 418, and more specifically are defined along a periphery of the lid 428. The cylindrical bottom container 420 and the lid 428 also define windows 435 which allow for egress of water vapor from the water dissipation device 412. The lid 428 can also be manufactured from a thermally conductive material to facilitate the cooling of the respiratory gases and increase water condensation.

A tubular breathable medium 436 is enclosed in the caged housing 418. The tubular breathable medium 436 may be pleated to increase the surface area of the breathable medium within the housing 418 and may also be perforated. The breathable medium 436 may also line at least a portion of an inside surface 438 of the side wall 422. The breathable medium 436 is formed of a material that is permeable to water vapor and impermeable to liquid water and other gases. The breathable medium 436 allows water vapor to exit the water dissipation device while eliminating the need to open the water dissipation device to empty a reservoir of water and, therefore, allows the system to remain closed.

Figure 15:
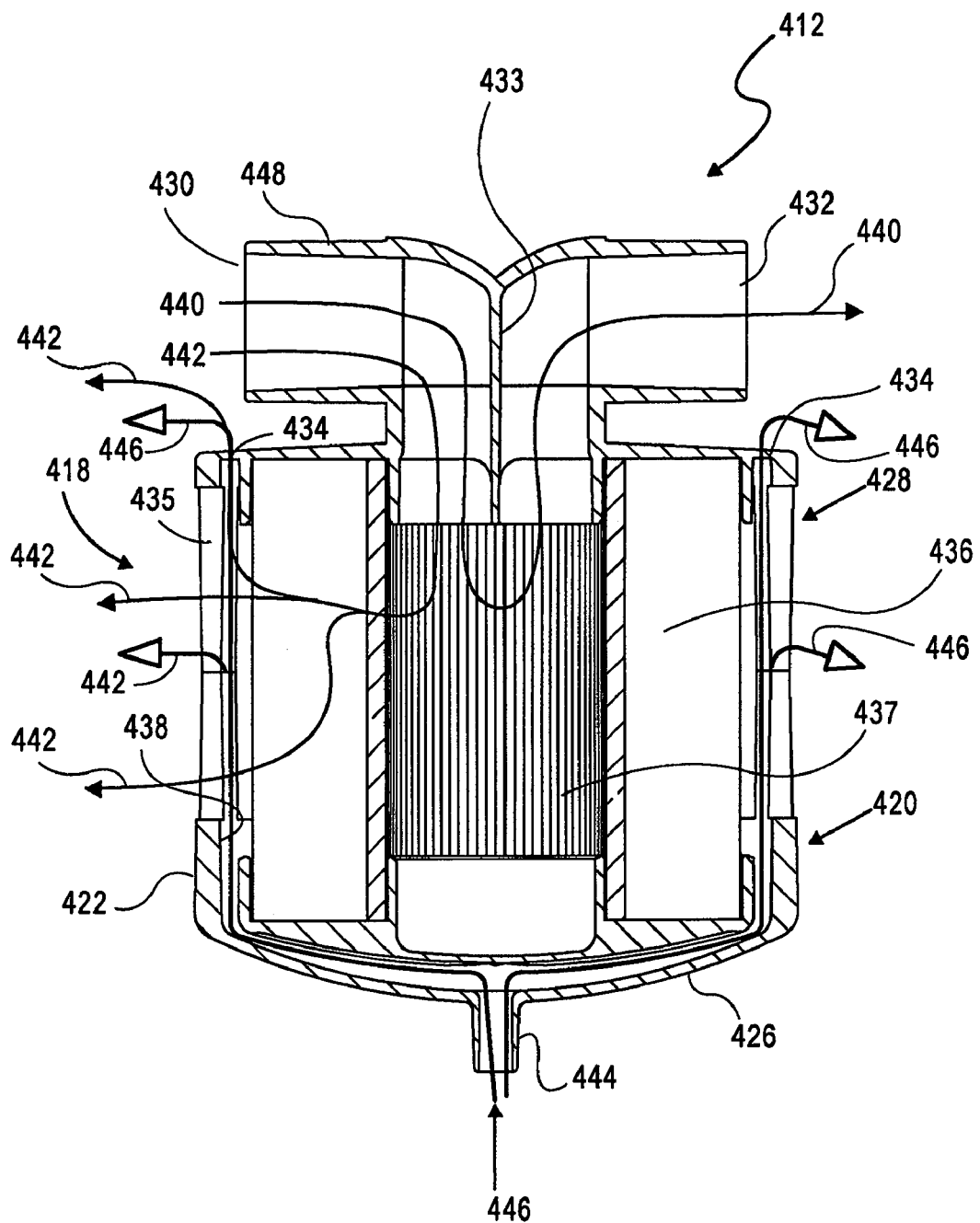
FIG. 15 is a cross-sectional view of the embodiment illustrated in FIG. 14.

FIG. 15 is a cross sectional view that further illustrates the embodiment of the water dissipation device illustrated in FIG. 14. The caged housing 418 defines a first flow path 440 of humidified gas between the entry port 430 and the exit port 432. In the first flow path 440, the humidified gas travels into the water dissipation device 412 via the entry port 430, through the housing 418 and exits the water dissipation device 412 via the exit port 432. The first flow path 440 therefore generally corresponds to the main flow path through the water dissipation device along the breathing circuit, except that in this embodiment, a partition or baffle element 433 extends in the housing 418 perpendicular to the axis through the entry and exit ports 430 and 432, which causes to further define the first flow path 440 to extend farther into the housing 418 and nearer to the channel 437 formed inside the annular breathable medium 436.

The housing also defines a second vapor path 442 that extends from the entry port 430 through the tubular breathable medium 436, and then out to either the water vapor vents 434 defined by the housing 418, or out of the housing 418 through the windows 435. However, liquid water and other gases cannot permeate the breathable medium 436 and exit through the windows 435.

Figure 16:
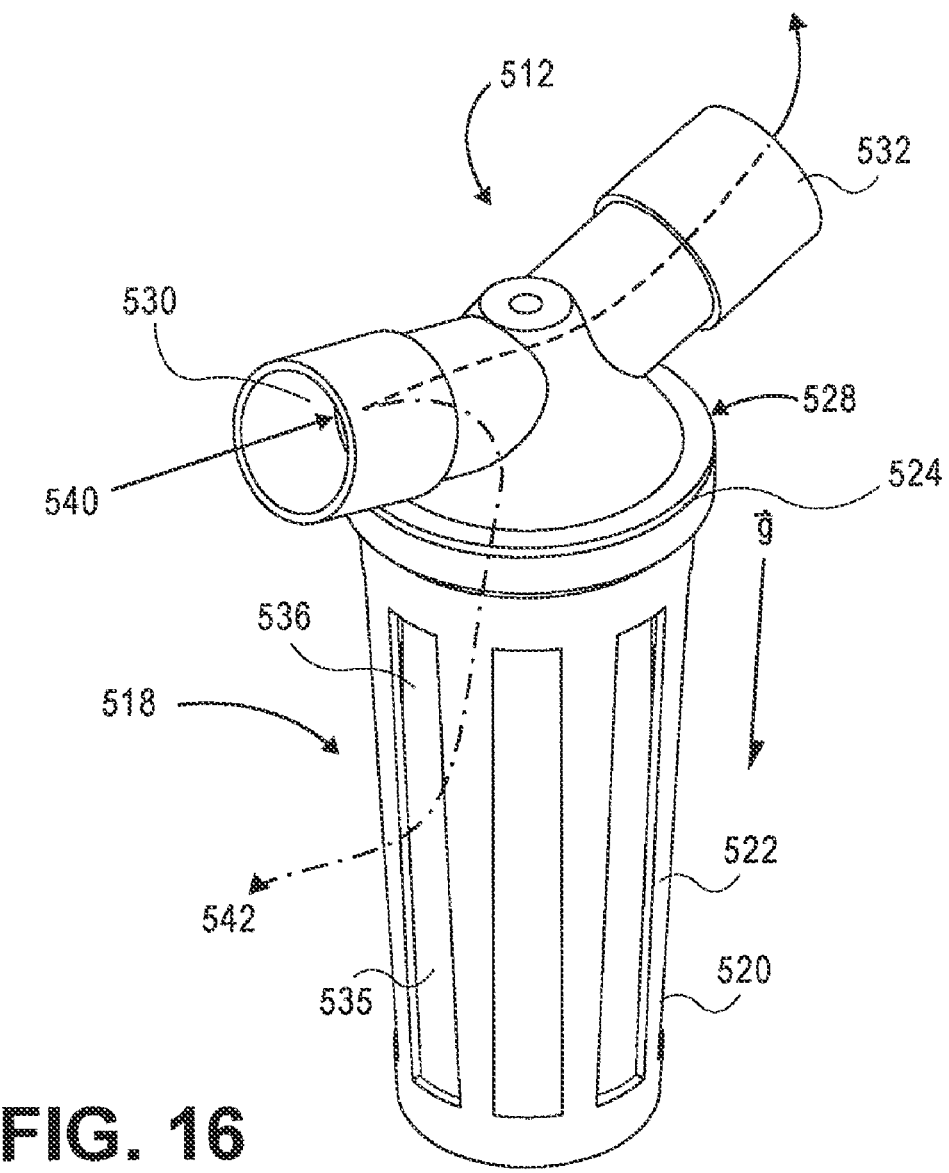
FIG. 16 is a three-quarter view illustrating another embodiment of the present invention.

Additionally, the bottom surface 426 of the outer housing 418 defines an orifice 444 to connect the water dissipation device 412 to an input air source. The housing 418, therefore, defines a third flow path 446 from the orifice 444 through the water dissipation device 412 and out through the water vapor vents 434, or out through the windows 435. The third flow path 446 provides a route for air introduced by the auxiliary compressed dry air input source to blow condensation off of the breathable medium to reduce liquid water collecting in the water dissipation device, and increase the efficiency of the breathable permeable medium. Another embodiment of the present invention is illustrated in FIG. 16. FIG. 16 is a three-quarter view illustrating a water dissipation device 512 according to another embodiment of the present invention. In this embodiment, the housing 518 includes a caged cylindrical bottom container 520 that has side wall 522 defining a top opening 524. The housing also includes the lid 528 that is mounted on the top opening 524. Additionally, the housing 518 defines an entry port 130 and an exit port 532. As shown in the embodiment in FIG. 16, the side wall 522 of the caged cylindrical bottom container 520 defines a plurality of windows 535. An annular or tubular breathable medium is encased inside the cage structure of the housing 518 against the sidewalls 522. A first flow path 540 flows from the entry port 540 through to the exit port 532, while a second water vapor flow path 542 flows from the entry port 530 down into the housing 518 though a central channel defined by the annular breathable medium 536, and then out through the breathable medium 536 and the windows 535.

Figure 17:
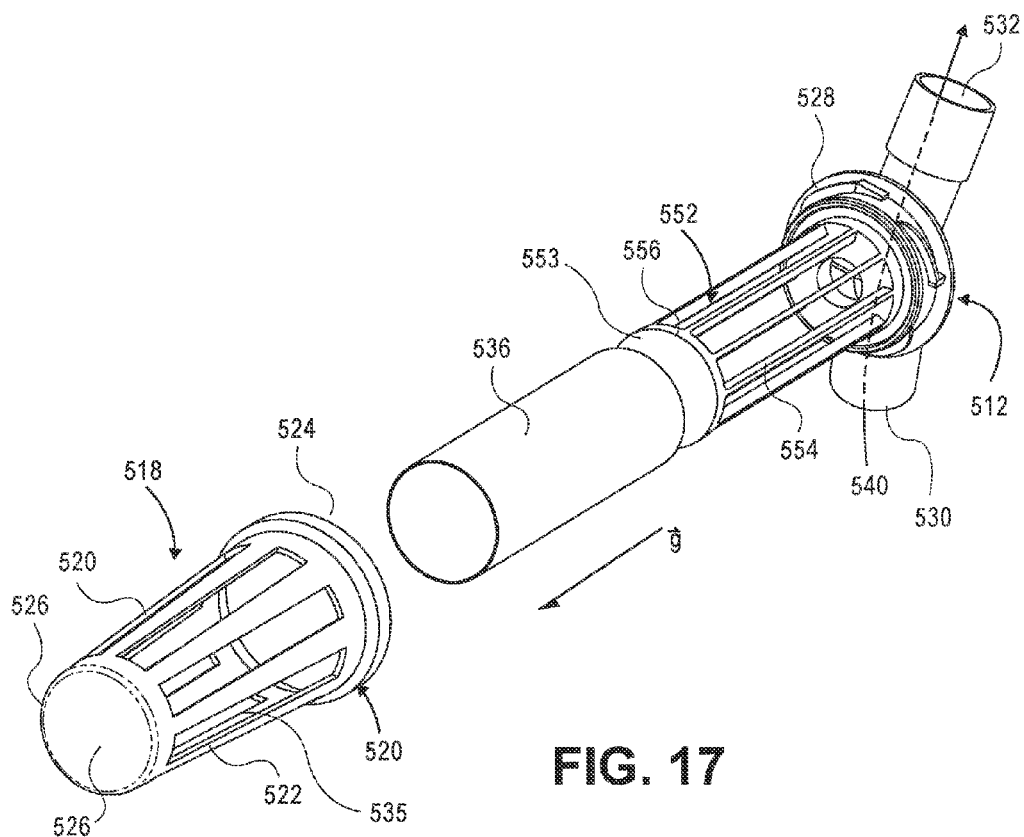
FIG. 17 is an exploded view of the embodiment illustrated in FIG. 16.

FIG. 17 is an exploded view of the embodiment illustrated in FIG. 16. FIG. 17 illustrates in more detail the structure of the housing 518 and the tubular breathable medium 536. Threads on the lid 528 as well as corresponding threads on the cylindrical bottom container 520 couple the lid 528 to the cylindrical bottom container 520.

Additionally, the lid 528 has a tubular cage 552 that extends into the cylindrical bottom container 520 of the housing 518. The tubular cage 552 has fins 554 that extend along the span of the housing 518. The fins 554 are separated by longitudinal openings or spaces that define water vapor vents 556 between the fins 554. The tubular cage 552 has a flat disk 553 to form a bottom for the tubular cage 552. A tubular breathable medium 536 is also disposed within the cylindrical bottom container 520, and it is positioned between the tubular cage 552 and the cylindrical bottom container 520 of the outer housing 518.

Figure 18:
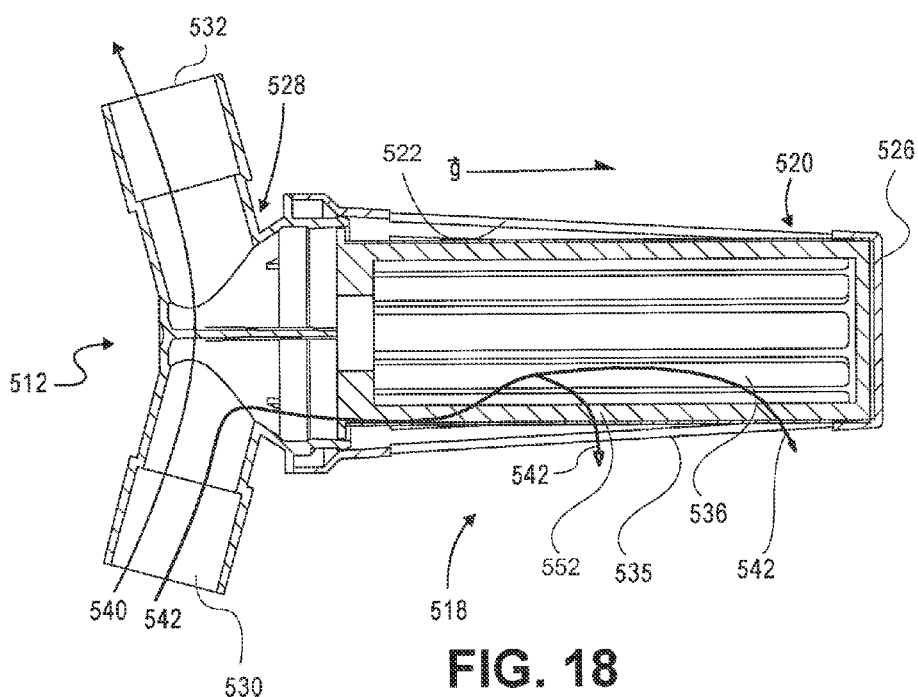
FIG. 18 is a cross-sectional view of the embodiment illustrated in FIGS. 16 and 17.

FIG. 18 is a cross sectional view of the embodiment illustrated in FIGS. 16 and 17. FIG. 18 illustrates the housing 518 and the breathable medium 536 in a fully assembled condition. The lid 528 and the cylindrical bottom container 520 couple together. The tubular cage 552 extends from a bottom surface of the lid 528 to the bottom surface 526 of the cylindrical bottom container 520. The tubular breathable medium 536 is disposed around and supported by the tubular cage 552.

A first flow path 540 is defined by the housing 518 and extends through the entry port 530, through the water dissipation device and through the exit port 532. The humidified gas generally flowing through the breathing circuit to which the device of the present invention is attached can therefore travel through the water dissipation device 512 via the first flow path 540. A second water vapor flow path 542 is also defined by the housing 518 and extends from the entry port 530 through the tubular breathable medium 536 and out of the water dissipation device 512 via the water vapor vents 556 defined by the fins 554 of the tubular cage 552 and out through the windows 535 defined by the caged cylindrical bottom container 520. Water vapor in the humidified gas may permeate the breathable medium 536 to exit through the water vapor vents 556, but liquid water, bacteria, viruses and other gases cannot permeate the breathable medium 536. An alternative embodiment of the device shown in FIGS. 17-18 could remove the bottom caged cylindrical housing body 520 such that the second flow path 542 flowed directly through the breathable medium 536 out to the surroundings.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A water dissipation device for a breathing circuit, comprising:
   a housing including at least a side wall, said side wall defining a top opening and enclosing an interior flow space within said housing, said side wall forming an exterior wall of the housing exposed to the surroundings outside of the device and said breathing circuit, the housing including a lid mounted over said top opening, the housing further defining an entry port and an exit port for coupling to a breathing circuit and defining at least a first flow path between said entry and exit ports for flow from the breathing circuit, said side wall being formed of a water vapor breathable medium that is permeable to water vapor and impermeable to liquid water, the housing further defining a second flow path extending from the entry port through the water vapor breathable medium and out of the water dissipation device, the second flow path providing a path for flow of water vapor out of the water dissipation device from the interior flow space through the side wall directly out to the surroundings outside of the device.

2. The water dissipation device of claim 1, further comprising:

a baffle on the lid extending into the housing between the entry and exit ports.

3. The water dissipation device of claim 2, wherein the baffle extends perpendicular to an axis between the entry and exit ports, and further defines the first flow path to extend into the housing.

4. The water dissipation device of claim 1, further comprising:

a cage structure in the housing, the water vapor breathable medium being disposed around the cage structure.

5. The water dissipation device of claim 4, wherein the water vapor breathable medium is supported by the cage structure.

6. The water dissipation device of claim 4, further comprising:

wherein the cage structure extends from a bottom surface of the lid to the bottom of the device.

7. The water dissipation device of claim 1, wherein the water vapor breathable medium is impermeable to gases other than water vapor and the water dissipation device as coupled to said breathing circuit forms a part of a closed breathing system.

8. The water dissipation device of claim 1, wherein the housing is configured to be coupled to a breathing circuit such that the housing and side wall extend substantially perpendicular and downwards from breathing circuit tubing to which the entry and exit ports are coupled, the housing being distinct from said breathing circuit tubing.

* * * * *